Dec. 30, 1958 R. W. CUMMING Plant Pat. 1,791
CHRYSANTHEMUM PLANT
Filed May 13, 1958
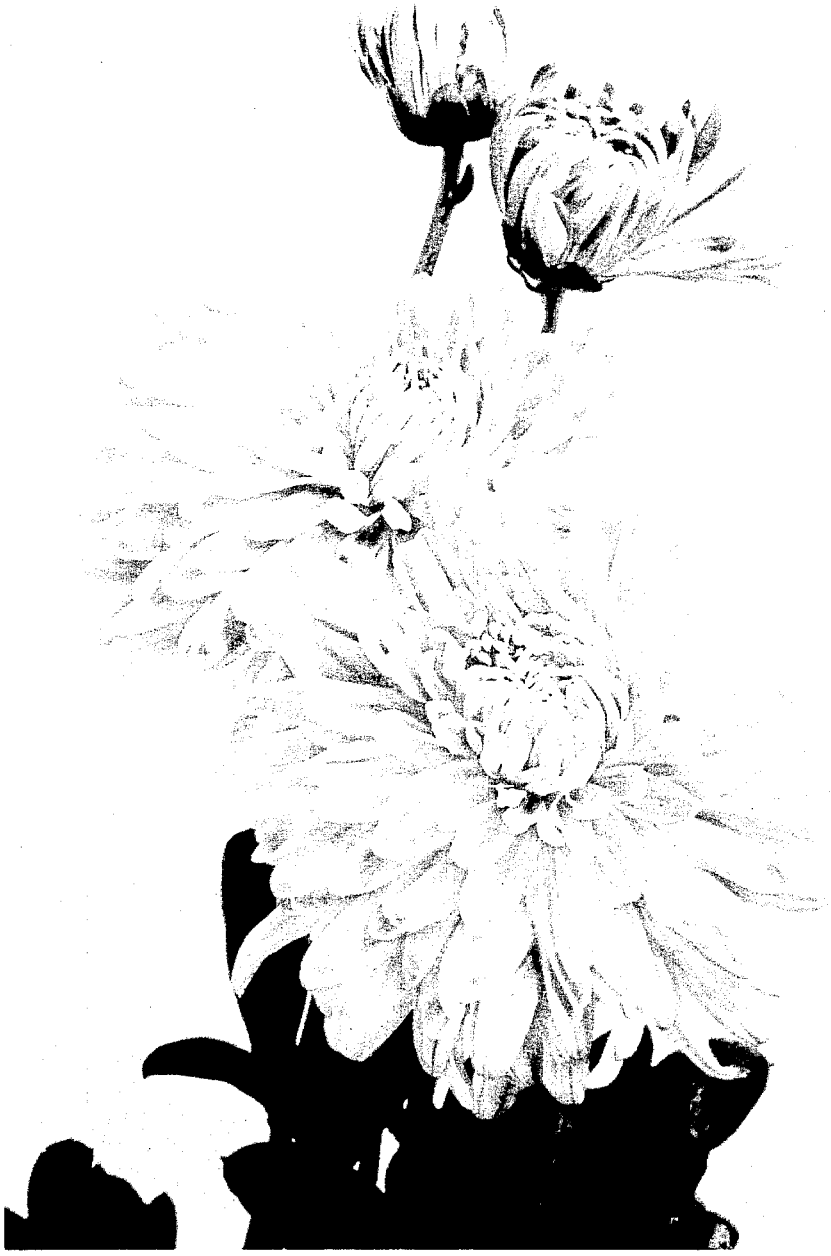
INVENTOR
Roderick W. Cumming
By Orville M. Kile
Plant Patent Agt.

United States Patent Office

Plant Pat. 1,791
Patented Dec. 30, 1958

1,791

CHRYSANTHEMUM PLANT

Roderick W. Cumming, Bristol, Conn., assignor to Bristol Nurseries, Inc., Bristol, Conn.

Application May 13, 1958, Serial No. 735,071

1 Claim. (Cl. 47—60)

My present invention relates to a new and distinct variety of chrysanthemum plant of the decorative class, which was originated by me, by means of self-pollinating an unamed seedling of unnamed bronze and pink ancestry of three previous generations.

The primary objective of this self-pollination was to produce a new chrysanthemum of intermediate, novel coloring, early period of display, and upright growth habit. This objective was achieved, along with the following outstanding characteristics displayed by the new variety:

(1) The large quantity of blossoms gracefully spaced on wiry, erect plants.

(2) The very healthy, glossy, deep green foliage which remains on the plant all the way to the ground.

(3) The supple stems for excellent cutting.

(4) The long period of productivity of flowers.

(5) The large size, decorative form, and shapely nature of the flowers.

(6) The distinctive flower coloring of Dawn Pink, initially Shell Pink, occasionally flushed Tangerine Orange at center.

The foregoing characteristics and distinctions definitely differentiate my new variety from its parents, as well as from all other varieties of its class of which I am aware.

Asexual reproduction of the new variety by top cuttings, performed by me at Bristol, Connecticut, shows that these characteristics and distinctions come true to form, and are established and transmitted through succeeding propagation.

The accompanying illustration shows typical specimens of the vegetative growth and flowers of my new chrysanthemum variety in various stages of development and in colors as nearly true as it is reasonably possible to make them by the medium used.

The following is a detailed description of my new variety, with color terminology and plate references in accordance with The Horticultural Colour Chart, issued by The British Colour Council. Where no references are given, ordinary dictionary meaning of the term is intended.

Classification: Decorative.

Parentage: Self-pollinated, unnamed seedling of unnamed bronze and pink ancestry.

Cold resistance: Winter hardy in central Connecticut under normal protection; flowers quite resistant to frost.

Health: No leafspot has ever developed in periods of alternating heat and wetness in late summer, although the variety nearest like it—Patricia Lehman (unpatented—has been discontinued in our gardens because it persistently develops leafspot under such conditions.

Blooming period: In the Bristol, Connecticut area, blooming starts about September 15 and continues until extreme freezing weather.

Productivity: This variety produces large quantity of blooms, gracefully spaced on stems.

*The plant*

Growth: Free, strong, upright, and graceful. Attains a height of from 30 to 36 inches.

Form: Rather tall, willowy, and with loose airy spacing of stems.

Stems: Supple, erect, and strong. Long for excellent cutting.

Foliage:

*Size.*—Normal, to 3 inches long.

*Quantity.*—Average. Remains on plant all the way to the ground.

*Form.*—Not deeply cut.

*Color.*—Dark green. Upper side, Parsley Green—962. Reverse side, Lavender Green 00761/1.

*Aspect.*—Glossy.

*The flower*

Bud:

*Color.*—Shell Pink to Rose Pink, as follows: When sepals first divide, Shell Pink 5/6. When petals begin to unfurl, Shell Pink 5/6/1. When half blown, inside of ray petal, Venetian Pink 420/1 to Rose Pink 427/1 after frosty weather. Reverse of petal, Rose Pink 427/1.

*Size.*—Moderately large.

*Shape.*—Flattened at first; opening slowly.

*Peduncle.* — Strong and upright; Leek Green, 000858/1.

Bloom:

*Borne.*—Singly.

*Size.*—Usually 3 to 3½ inches in diameter. Often larger.

*Form.*—Composite flower of decorative type. Center is composed of many bunched, inwardly curved, narrow ray-flowers, with approximately 100 strap-like ray-flowers extending outwardly in almost horizontal position.

*Petalage.*—Very double.

*Texture.*—Firm when placed in water.

*Fragrance.*—Lightly characteristic of chrysanthemums

*Color.*—Center of flower, Tangerine Orange 9/2 as occasional flush. Outer petals or ray-flowers, Cadmium Orange 8/3 at center. Inside of petals, Dawn Pink 523/3 at base, with upper part Venetian Pink 420/1. Reverse of petals, Dawn Pink 523/1.

*Petals or ray-flowers.*—Firm; strap-like; length, 1½ to 1¾ inches.

*Flower stem.*—Strong, erect, but not rigidly stiff.

*Comparison*

The known variety most like my new variety is Patricia Lehman (unpatented), the following being the most outstanding differences:

(1) My new variety begins flowering from 7 to 10 days earlier than Patricia Lehman.

(2) My variety has longer flower stems for better cutting.

(3) My variety grows erectly to a height of 2½ to 3 feet, whereas Patricia Lehman tends to droop badly in adverse weather.

(4) My variety has never shown any leafspot on its foliage in periods of alternating heat and wetness in late summer, whereas Patricia Lehman persistently develops leaf spot under such conditions.

(5) The color of the flower of my new variety is pronouncedly coral-pink, as compared to geranium-pink of Patricia Lehman, and has a more pleasing sparkle.

(6) The form of my variety's flower is more rounded and full.

Having thus disclosed my invention, I claim:

The new and distinct variety of chrysanthemum plant of the hardy decorative type, substantially as herein shown and described, characterized particularly as to novelty by its airy grace of plant growth; its very healthy, glossy, dark green foliage which remains on the plant all the way to the ground; its erect, strong and wiry stems; its very early period of flower display; and its excellent productivity of large, long-lasting, decorative flowers with general color tonality of Dawn Pink, occasionally flushed Tangerine Orange.

No references cited.